United States Patent [19]

Sittler

[11] Patent Number: 5,707,150
[45] Date of Patent: Jan. 13, 1998

[54] APPARATUS FOR COMPUTING BTU CONTENT IN A SAMPLE OF GAS

[75] Inventor: Fred C. Sittler, Victoria, Minn.

[73] Assignee: Rosemount Analytical Inc., La Habra, Calif.

[21] Appl. No.: 531,218

[22] Filed: Sep. 19, 1995

[51] Int. Cl.⁶ .................................................. G01N 25/22
[52] U.S. Cl. .............................. 374/36; 374/39; 374/40
[58] Field of Search ................................ 374/36, 39, 40, 374/54

[56] References Cited

U.S. PATENT DOCUMENTS

| | | | |
|---|---|---|---|
| 3,112,639 | 12/1963 | Maxwell | 73/23 |
| 3,140,615 | 7/1964 | Broerman | 73/422 |
| 3,560,160 | 2/1971 | Lanneau | 23/232 |
| 3,701,280 | 10/1972 | Stroman | 73/194 M |
| 4,030,369 | 6/1977 | Etheridge | 73/422 GC |
| 4,070,913 | 1/1978 | Roof | 73/422 GC |
| 4,215,563 | 8/1980 | Clardy et al. | 73/23.1 |
| 4,345,463 | 8/1982 | Wilson et al. | 73/190 CV |
| 4,511,262 | 4/1985 | Arcara | 374/37 |
| 4,584,868 | 4/1986 | Jacobsen et al. | 73/23 |
| 4,614,721 | 9/1986 | Goldberg | 436/147 |
| 4,650,499 | 3/1987 | Scott | 55/18 |
| 4,869,282 | 9/1989 | Sittler et al. | 137/15 |
| 4,869,597 | 9/1989 | Christopher | 374/37 |
| 4,869,873 | 9/1989 | Klein et al. | 422/51 |
| 5,012,432 | 4/1991 | Stetter et al. | 364/557 |
| 5,152,176 | 10/1992 | Bryselbout et al. | 73/23.41 |
| 5,166,076 | 11/1992 | Muller et al. | 436/161 |
| 5,235,844 | 8/1993 | Bonne et al. | 73/24.01 |
| 5,265,417 | 11/1993 | Visser et al. | 60/277 |
| 5,360,266 | 11/1994 | Lenfers et al. | 374/36 |
| 5,392,634 | 2/1995 | Asano et al. | 73/23.42 |
| 5,551,282 | 9/1996 | Vander Heyden | 73/30.03 |

Primary Examiner—George M. Dombroske
Assistant Examiner—Joseph L. Felber
Attorney, Agent, or Firm—Westman, Champlin & Kelly, P.A.; S. Koehler

[57] ABSTRACT

An apparatus for measuring the BTU content of a gas includes a source of combustion air, a detector and a sample loop or tube connected to a six-port switching valve. The switching valve allows accurate and repeatable quantities of the gas to be obtained and mixed with the combustion air. In a second embodiment, the apparatus includes a second switching valve to obtain samples of the gas at a second pressure and calculate the BTU content at the second pressure. By measuring the BTU content at two different pressures, a quantity related to the volumetric flow of the gas between the two pressures can also be calculated.

17 Claims, 3 Drawing Sheets

5,707,150

APPARATUS FOR COMPUTING BTU CONTENT IN A SAMPLE OF GAS

BACKGROUND OF THE INVENTION

The present invention relates to gas flow measurement apparatuses. More particularly, the present invention relates to a measurement apparatus that obtains a precise, repeatable sample of a combustible gas to measure the BTU (British Thermal Unit) content of the gas. A measurement apparatus and method to obtain a quantity related to the volumetric flow of a gas are also disclosed.

Increasing attention has been focused upon quantitatively measuring natural gas flowing in a pipeline. Since the primary purpose for supplying natural gas is to generate heat for various industrial or residential purposes, the gas industry has recognized that the BTU content of the natural gas flowing in the pipeline is one of the most important factors in determining the value of the natural gas. The BTU content of natural gas typically varies between 900 and 1,200 BTU/Ft$^3$.

However, since natural gas is a compressible fluid, the volume being a function of temperature and pressure, the measured BTU content of the flowing natural gas must be related to a standard volume at a specified temperature and pressure. To translate the calculated volume of the flowing pressure and temperature of the gas to a base pressure and base temperature, it is customary to apply the law for an ideal gas. However, all gasses deviate from the ideal gas law to a greater or lessor extent. This deviation has been termed by the industry as "supercompressibility factor". The supercompressibility factor is particularly appreciable at higher pressures. Therefore, this factor, along with the BTU content of the natural gas at a specified pressure and temperature, must be taken into account in order to calculate the value of the flowing gas.

A simple, low-cost and reliable measuring apparatus that can measure the BTU content of natural gas with high accuracy is desirable. An apparatus that can further measure and calculate a suitable quantity to account for the supercompressibility factor of natural gas is also desirable.

SUMMARY OF THE INVENTION

An apparatus for measuring the BTU content of a gas includes a source of combustion air, a detector, and a sample loop or tube connected to a switching valve. The switching valve allows accurate and repeatable quantities of the gas to be obtained and mixed with the combustion air. In a second embodiment, the apparatus includes a second switching valve to obtain samples of the gas at a second pressure and calculate the BTU content at the second pressure. By measuring the BTU content at two different pressures, a quantity related to the volumetric flow of the gas between the two pressures can also be calculated.

In the embodiment disclosed, the source of combustion air and the detector are connected to the switching valve having six ports. Each port is selectively fluidly connected to two of the six ports wherein a first port is connected to the source of combustion air and is selectively fluidly connected to a second port. The second port is fluidly connected to the detector and a third port. A fourth port is connectable to the source of gas and selectively fluidly connected to the third port and a fifth port connectable to a pressure source less than the source of gas. A sixth port is selectively fluidly connected to the second port and the fifth port. A sample tube is connected to the third port and the sixth port.

The detector senses the heat content of a sample volume of the gas and provides a representative signal to a computer. The computer receives the signal and records a representative value of the heat content on a suitable recorder. The computer further provides control signals to control operation of the switching valve.

Another aspect of the present invention includes a method for calculating a quantity related to volumetric flow of the gas. The method includes measuring a quantity of heat generated from a volume of gas at a pressure, and calculating the quantity related to volumetric flow of the gas from the measured quantity of heat.

DETAILED DESCRIPTION OF THE PREFERRED EMBODIMENTS

Figure 1:
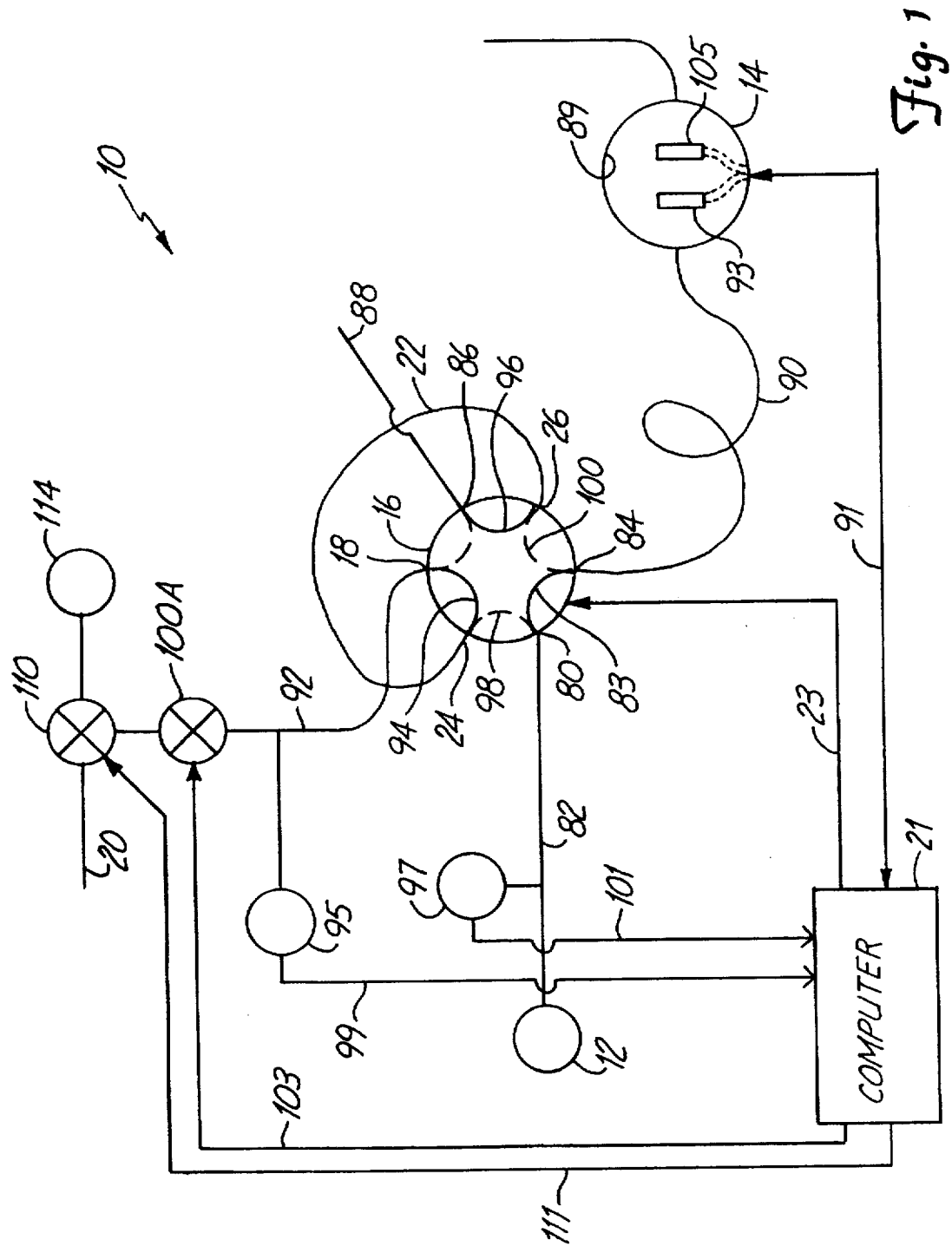
FIG. 1 is a schematic block diagram of a BTU measuring apparatus according to the present invention.

A BTU measuring apparatus of the present invention is illustrated generally at 10 in FIG. 1. The BTU measuring apparatus includes a source of combustion air 12 and a detector 14 connected to a multi-port switching valve assembly 16 described below in detail. A port 18 of the multi-port switching valve assembly 16 is connectable to a source of the combustible gas to be sampled through a line 20. The BTU measuring apparatus 10 also includes a sample loop or tube 22 connected between two ports 24 and 26 of the multi-port switching valve assembly 16. A computer 21 controls the multi-port switching valve assembly 16 via a signal line 23 so that small, accurate and repeatable quantities of the gas to be measured are periodically obtained in the sample tube 22. The computer 21 then operates the multi-port switching valve assembly 16 to expel the sample of combustible gas from the sample tube 22 to the detector 14 by controlling the flow of combustion air to the detector 14.

Figure 2:
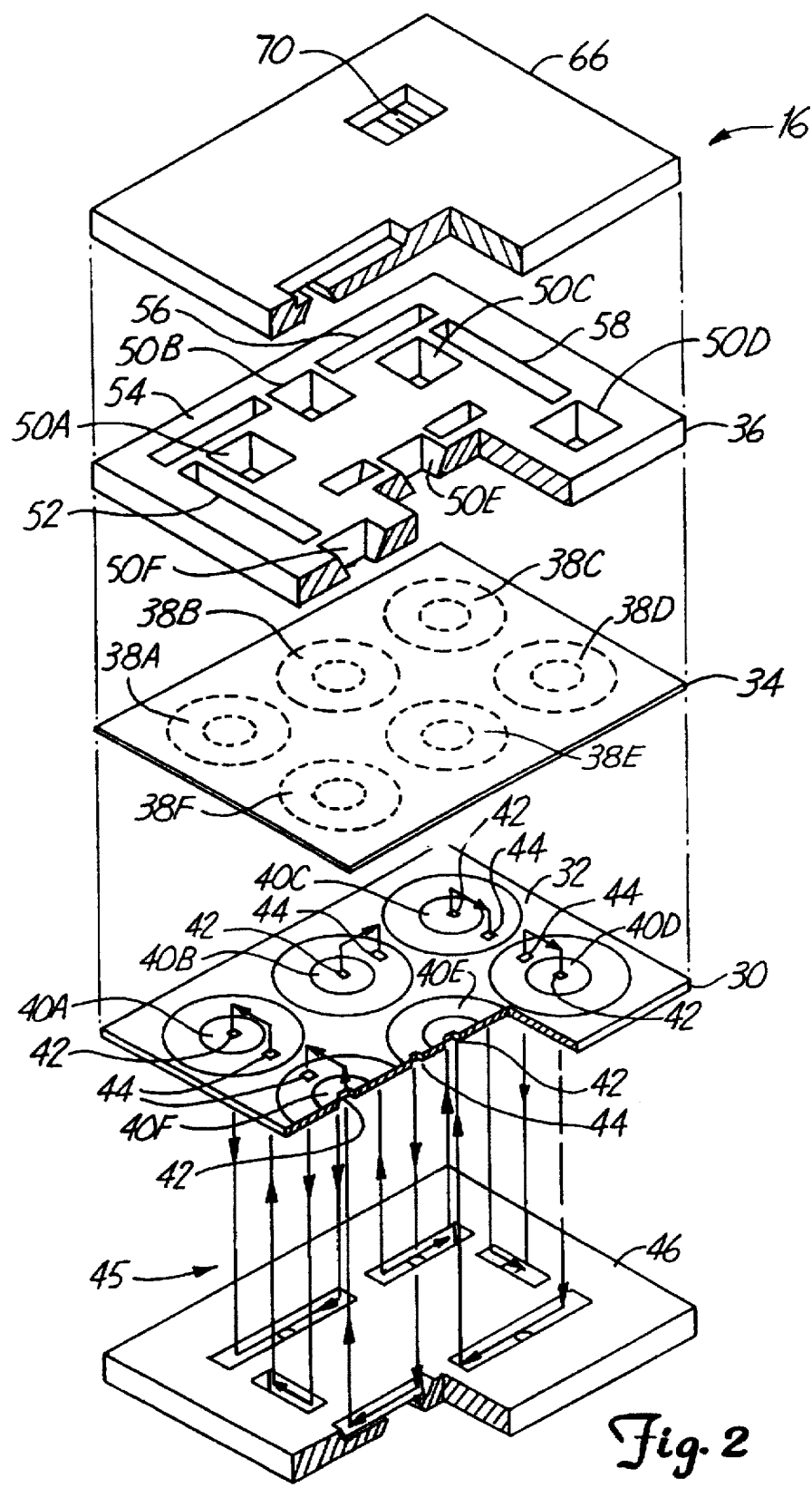
FIG. 2 is an exploded perspective view of a prior art six-port switching valve assembly with portions in section.

A preferred multi-port switching valve assembly 16 useable in the preferred embodiment is illustrated in FIG. 2 and described in detail in U.S. Pat. No. 4,869,282 and in abandoned application Ser. No. 08/346,346, both of which are incorporated herein by reference. Briefly, the multi-port switching valve assembly 16 comprises a sandwich construction of several individual layers bonded together, including: a valve seat wafer or layer 30 having an upper valve seat surface 32; a flexible layer 34; and a stop layer 36 having means for controlling deflection of individual diaphragm portions 38A, 38B, 38C, 38D, 38E and 38F included in the flexible layer 34.

Each of the diaphragm portions 38A-38F are aligned with corresponding valve seats 40A, 40B, 40C, 40D, 40E and 40F formed on the upper surface valve seat surface 32. Each diaphragm portion 38A-38F seals two valve ports indicated at 42 and 44 in each of the valve seats 40A-40F, respectively. Each of the valve ports 42 and 44 fluidly connect to a lower channeling layer 46, which interconnects each of the valve sections as illustrated by arrows 45 to two adjacent valve sections.

Actuation gas flow through the multi-port switching valve assembly 16 is controlled through control ports 50A, 50B, 50C, 50D, 50E and 50F which control deflection of each of the diaphragm portions 38A-38F with suitable pressure differentials applied thereto. Channels, such as illustrated at 52, 54, 56, and 58 formed in the stop layer 36 and additional channels formed in an upper layer 66 direct actuating fluid to the control ports 50A–50F.

Preferably, the layers 30, 36, 46 and 66 of the multi-port switching valve assembly 16 are micromachined, such as through the use of known photolithography techniques including etching processes, or through the use of electrostatic discharge machining (EDM), or, if glass layers are utilized, through the use of molding or laser machining processes when the glass layers are formed to create any necessary channels.

The materials can be any desired semi-conductor material or other brittle materials that are non-reactive to the gases used. Silicon is a useful material for the valve seat layer 30, the stop layer 36, the lower channeling layer 46, and the upper layer 66. Other materials such as glass or sapphire also can be used for one or more of the layers. The layers do not have to be all one type of material.

For purposes of the present invention, the multi-port switching valve assembly 16 is illustrated schematically in FIG. 1. As illustrated and described above, the multi-port switching valve assembly 16 has, preferably, six ports wherein each port is selectively fluidly connected separately to two other ports. A first position is illustrated with solid lines and a second position is illustrated with dashed lines. In the embodiment illustrated, a line 82 connects a first port 80 to the source of combustion air 12. The first port 80 is selectively fluidly connected to a second port 84 and the port 24 (hereinafter "the third port"). Preferably, a mixing column 90 connects the second port 84 to the detector 14. The port 18 (hereinafter "the fourth port") connects to the line 20 to receive the gas to be sampled and is selectively fluidly connected to the third port 24 and a fifth port 86. The fifth port 86 connects to a pressure source, herein embodied as a vent 88 to atmospheric pressure, that has a pressure less than the pressure of the gas in the line 20. The port 26 (hereinafter "the sixth port"), is selectively fluidly connected to the second port 84 and the fifth port 86. The sample tube 22 connects to the third port 24 and the sixth port 26.

The BTU measuring apparatus 10 operates as follows. Referring first to the operating state of the multi-port switching valve assembly 16 illustrated with solid lines, combustion air from the combustion air source 12 flows through the multi-port switching valve 16 in a channel 83 into the mixing column 90 which connects the multi-port switching valve assembly 16 to the detector 14.

In the preferred embodiment, the detector 14 has an inner chamber 89 in which a heterogeneous catalytic sensor 93 is disposed. The catalytic sensor 93 has a coil of fine platinum wire over which a catalytic (platinum on alumina) surface has been formed. This type of sensor is well known and operates when the computer 21 passes a current through the platinum wire via a signal line 91 to heat the catalytic surface. When a combustible gas comes into contact with the heated catalytic sensor 93, the catalytic surface reacts with the gas producing some heat. The heat is proportional to the heat of combustion of the hydrocarbon gas and the concentration of the gas.

Some of the heat generated at the surface of the detector 14 is lost, while another portion is transferred to the detector 14. The portion of the heat transferred to the catalytic sensor 93 causes a subsequent increase in temperature, which in turn, causes an increase in the resistance of the platinum wire. By measuring the change in resistance of the platinum wire with the computer 21, for example, by connecting the platinum wire as one leg in a Wheatstone bridge circuit, the BTU content of the combustible gas can be measured.

Since only combustion air is flowing into the detector 14 at this point, the catalytic sensor 93 does not register any change in temperature because no reaction is occurring. In this position, the third port 24 of the multi-port switching valve assembly 16 is connected to the fourth port 18 through a channel 94 and the sixth port 26 is connected to the fifth port 86 through a channel 96, which in turn, connects the sample tube 22 to the line 20 and the vent 88.

In this position, the gas from the line 20 flows into the multi-port switching valve assembly 16, through the channel 94, through the sample tube 22, through the channel 96 and out the vent 88. The sample tube 22 provides a small, accurate, repeatable quantity of gas to be measured. This quantity of gas is provided to the detector 14 when the multi-port switching valve assembly 16 is switched to the operating state illustrated with dashed lines. In this position, the source of combustion air 12 is now connected to the sample tube 22 through a channel 98, while an opposite end of the sample tube 22 is connected to the mixing column 90 through a channel 100. The combustion air from the combustion air source 12 pushes the quantity of gas in the sample tube 22 into the mixing column 90 where it mixes with the combustion air, the combination of which is provided to the detector 14.

The apparatus 10 calculates the BTU content per unit volume of the sampled gas. To correct for small pressure differences from the line 20 to the fixed volume of the sample tube 22, gauge or absolute pressure transducers 95 and 97 are disposed in the line 20 and the line 82, respectively, and provide suitable signals to the computer 21 on signal lines 99 and 101, respectively. Measuring the combustion air pressure is also useful, since loss of pressure in the combustion air source 12 can result in a high concentration of natural gas in the detector 14, which can damage the catalytic sensor 93.

In a preferred embodiment, the detector 14 includes a reference sensor 105 also disposed in the inner chamber 89. The reference sensor 105 is similar to the catalytic sensor 93 but does not have a catalytic outer surface. The reference sensor 105 receives current from the computer 21 to maintain the reference sensor 105 at a selected elevated temperature, preferably substantially the same as the catalytic sensor 93. The computer 21 monitors the power required to maintain the reference sensor 105 at the selected temperature and subtracts the corresponding value from that required for the catalytic sensor 93 thereby correcting for heat loss or gain due to ambient temperature and gas flow changes. An embodiment of the apparatus 10 illustrated in FIG. 1 provides "atmospheric standardization" of the gas sample. This is accomplished by venting the sample tube 22 to atmospheric pressure after it has been filled with the gas to be measured. In the embodiment illustrated, a valve 100 is disposed in a line 92 between the fourth port 18 and the line 20 and receives control signals from the computer 21 on a signal line 103. The valve 100A is open when the gas to be sampled is flowing from the line 20 through the sample tube 22 and out the vent 88. Just prior to switching the multi-port switching valve assembly 16 to connect the sample tube 22 to the source of combustion air 12, the computer 21 transmits a suitable signal to close the valve 100. In this state, the sample tube 22 is still connected to the vent 88 so that the gas in the sample tube 22 bleeds out of the vent 88 until the pressure in the sample tube 22 substantially equals atmospheric pressure. The multi-port switching valve assembly 16 is then operated to connect the source of combustion air 12 and the mixing column 90 to the sample tube 22 and expel the standardized gas sample in the sample tube 22 to the detector 14.

Another feature of the apparatus 10 illustrated in FIG. 1 provides periodic samples of a known calibration gas to ensure proper operation of the detector 14. In the embodiment illustrated, a valve 110 is disposed between the fourth port 18, the line 20 and a source of calibration gas indicated at 114. The valve 110 receives control signals from the computer 21 on a signal line 111. In a first operating state, the valve 110 fluidly connects the line 20 to the fourth port 18 to provide the gas to be measured to the multi-port switching valve assembly 16 in the manner described above. Periodically, the computer 21 switches the valve 110 to a second operating state where the line 20 is disconnected from the fourth port 18 and the source of calibration gas 114 is fluidly connected to the fourth port 18. In this operating state, at least one sample of a calibration gas rather than the gas to be measured is provided to the detector 14. The sample or samples of calibration gas are obtained in the sample tube 22 and mixed with the combustion air in the manner described above.

Figure 3:
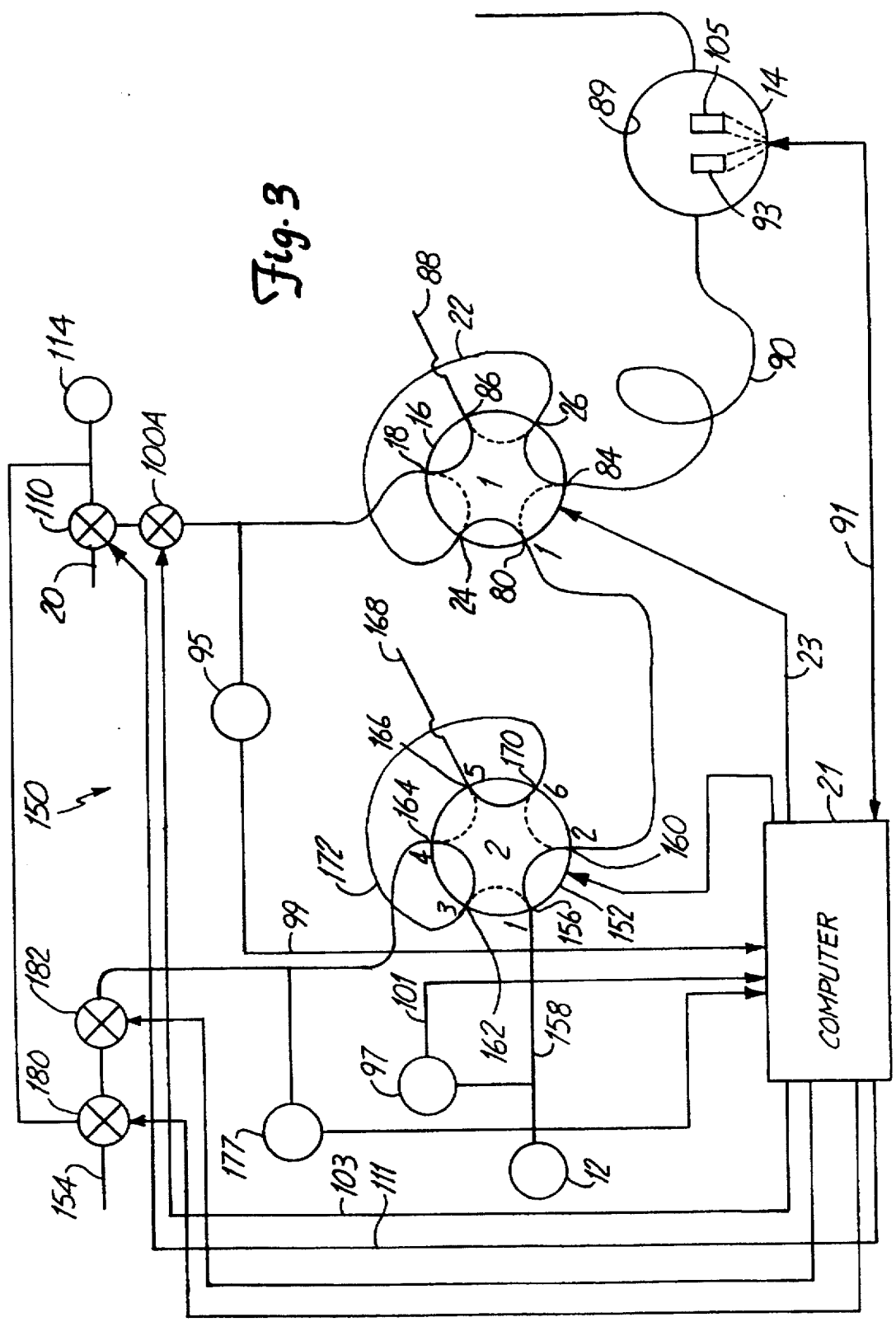
FIG. 3 is a schematic block diagram of a second embodiment of a BTU measuring apparatus according to the present invention.

A second embodiment of the BTU measuring apparatus 10 of the present invention is illustrated generally at 150 in FIG. 3. The apparatus 150 includes the multi-port switching valve 16, the computer 21 and a second multi-port switching valve 152. The apparatus 150 measures the BTU content of the gas to be sampled from the line 20 and a second line indicated at 154. As described below, a quantity related to the volumetric flow of the gas between the line 20 and the line 154 is made by comparing the BTU per unit volume at the two corresponding pressures.

In the embodiment illustrated, the multi-port switching valve 152 has six ports wherein each port is selectively fluidly connected to two other ports of the switching valve. A first port 156 connects to the source of combustion air 12 through a line 158. The first port 156 is selectively fluidly connected to a second port 160 and a third port 162. The second port 160 fluidly connects to the first multi-port switching valve assembly 16 at port 80. A fourth port 164 is connectable to the line 154 and is selectively fluidly connected to the third port 162 and a fifth port 166. The fifth port 166 connects to a pressure source, herein embodied as a vent 168 to atmospheric pressure that is less than the pressure of the line 154. A sixth port 170 is selectively fluidly connected to the second port 160 and the fifth port 166. A second sample tube 172 connects to the third port 162 and the sixth port 170.

The apparatus 150 alternately samples the gas from the first line 20 and the second line 154. Arbitrarily, beginning with the multi-port switching valve assemblies 16 and 152 in the operating positions indicated with solid lines, combustion air from the combustion air source 12 flows into the first port 156 of the second multi-port switching valve assembly 152 and out through the second port 160. The combustion air flows into the first port 80 of the first multi-port switching valve assembly 16 to expel a quantity of gas out of the sample tube 22 and into the mixing column 90 and to the detector 14. During this time, a sample of gas from the line 154 is obtained in the second sample tube 172 since the third port 162 is connected to the fourth port 164 and the sixth port 170 is connected to the fifth port 166 that leads to the vent 168. When the multi-port switching valve assemblies 16 and 152 switch to the operating positions shown with dashed lines, the combustion air source 12 is connected to the second sample tube 172 to expel the sample out of the second sample tube 172 and into the first port 80 of the first multi-port switching valve assembly 16. At this time, the first port 80 of the first multi-port switching valve assembly 16 is connected to the second port In this manner, the sample from the second sample tube 172 is provided through the first multi-port switching valve assembly 16 and into the mixing column 90 to the detector 14. While the sample from the second sample tube 172 is being transferred to the detector 14, a sample from the line 20 is being obtained in the sample tube 22 since the fourth port 18 of the first multi-port switching valve assembly 16 is connected to the third port 24 and the sixth port 26 is connected to the fifth port 86 which leads to the vent 88.

The apparatus 150 calculates the BTU content per unit volume of the sampled gas from each of the lines 20 and 154. The gauge or absolute pressure transducers 95, 97 and 177 are used to correct for small pressure differences from the lines 20 and 154 to the fixed volumes of the sample tubes 22 and 172. A valve 180 connected to the fourth port 164 of the second switching valve 152, the source of calibration gas 114 and the line 154 selectively connects the second switching valve 152 to the source of calibration gas 114 and the line 154. A valve 182 connected to the fourth port 164 of the second switching valve 152 is used to standardize the gas sample in the sample tube 172 like the valve 100A described above.

The apparatus 150 can be used to calculate a quantity related to the supercompressibility ratio of the sampled gas at two different pressures. This information is of value to pumping and distribution stations.

As is well known, the supercompressibility ratio, S, is defined relative to Standard Temperature and Pressure (STP). Between any two pressures $P_1$ and $P_2$ the following relationship exists for volumetric flow:

$$S_1 P_1 V_{f1} = P_0 V_{f0} = S_2 P_2 V_{f2} \qquad \text{Eq. 1}$$

where $S_1$ is the supercompressibility ratio and $V_{f1}$ is the volumetric flow at the first pressure $P_1$, $S_2$ is the supercompressibility ratio and $V_{f2}$ is the volumetric flow at the second pressure $P_2$, and $P_0$ and $V_{f0}$ are at STP.

Equation 1 can be rewritten as, $$P_1 V_{f1} = (S_2/S_1) P_2 V_{f2} \qquad \text{Eq. 2}$$

which demonstrates that to make an accurate conversion of volumetric flow from $P_1$ to $P_2$, the quantity $S_2/S_1$ must be determined.

As is well known, any gas deviates from the ideal gas law by a quantity, Z, also known as the compressibility factor, which can be represented as follows:

$$Z = PV/MR_g T \qquad \text{Eq. 3}$$

where P is the pressure of the gas, V is the volume of the gas, T is the temperature of the gas, M is the number of moles of the gas and $R_g$ is the molar gas constant.

The apparatus 150 measures the heat, H, generated by M moles of gas with a Q heat value, which can be represented as:

$$H = MQ \qquad \text{Eq. 4}$$

and which can be substituted into Eq. 3 to yield:

$$PV = ZHR_g T/Q \qquad \text{Eq. 5}$$

Hence, for two pressures $P_1$ and $P_2$, and since the gas is the same at the two pressures where:

$$R_{g1} = R_{g2} = R_g \text{ and } Q_1 = Q_2 = Q$$

and T is constant, $$P_1V_1/Z_1H_1 = R_sT/Q = P_2V_2/Z_2H_2 \qquad \text{Eq. 6}$$

which can be rewritten as follows:

$$(H_2/H_1)(P_1V_1/P_2V_2) = Z_1/Z_2 = S_2/S_1 \qquad \text{Eq. 7}$$

where, $H_1$—heat measured from a sample of gas from line 20

$H_2$—heat measured from a sample of gas from line 154

$P_1$—pressure of line 20

$P_2$—pressure of line 154

$V_1$—volume of sample tube 22

$V_2$—volume of sample tube 172

Thus, the apparatus 150 can calculate the quantity $S_2/S_1$ from the measured and known parameters $H_1$, $H_2$, $P_1$, $P_2$, $V_1$, and $V_2$.

Although the present invention has been described with reference to preferred embodiments, workers skilled in the art will recognize that changes may be made in form and detail without departing from the spirit and scope of the invention.

What is claimed is:

1. An apparatus for measuring the BTU content of a sample of gas from a source of gas, the apparatus comprising:

a source of combustion air;

a switching valve having six ports, each port being selectively fluidly connected to two of the six ports, wherein a first port is connected to the source of combustion air and is selectively fluidly connected to a second port and a third port, a fourth port connectable to the source of gas and selectively fluidly connected to the third port and a fifth port connectable to a pressure source of a pressure less than that of the source of gas, and a sixth port selectively fluidly connected to the second port and the fifth port;

a sample tube connected to the third port and the sixth port;

a detector, connected to the second port, for sensing the heat content of a sample volume of the gas; and a computer receiving a signal from the detector representative of the heat content of the sample volume of gas and operably connected to the switching valve.

2. The apparatus of claim 1 wherein the source of gas includes a first line having the gas at a first pressure and a second line having the gas at a second pressure, the fourth port being connectable to the first line, and wherein the pressure source has a pressure less than that of the first line, and the apparatus further comprising a second switching valve connected to the first port of the first-mentioned switching valve, the second switching valve selectively fluidly connecting the first port of the first-mentioned valve to the source of combustion air and the second line.

3. The apparatus of claim 2 wherein the second switching valve has six ports, each port being selectively fluidly connected to two of the six ports, wherein a first port of the second switching valve is connected to the source of combustion air and is selectively fluidly connected to a second port of the second switching valve fluidly connected to the first port of the first-mentioned switching valve and a third port of the second switching valve, a fourth port of the second switching valve connectable to the second line and selectively fluidly connected to the third port of the second switching valve and a fifth port of the second switching valve connectable to a second pressure source of a pressure less than that of the second line, and a sixth port of the second switching valve selectively fluidly connected to the second port of the second switching valve and the fifth port of the second switching valve; and the apparatus further comprising a second sample tube connected to the third port of the second switching valve and the sixth port of the second switching valve.

4. The apparatus of claim 3 wherein a volume of the first-mentioned tube is different from a volume of the second tube.

5. The apparatus of claim 3 and further comprising a source of calibration gas and a third switching valve connected to the fourth port of the first-mentioned switching valve, the source of calibration gas and connectable to the first line, the third switching valve selectively fluidly connecting the first-mentioned switching valve to the source of calibration gas and the first line.

6. The apparatus of claim 3 and further comprising a source of calibration gas and a third switching valve connected to the fourth port of the second-mentioned switching valve, the source of calibration gas and connectable to the second line, the third switching valve selectively fluidly connecting the second switching valve to the source of calibration gas and the second line.

7. The apparatus of claim 3 and further comprising:

a third switching valve connected to the fourth port of the first-mentioned switching valve and connectable to the first line, the third switching valve selectively fluidly connecting the first-mentioned switching valve to a source of standard pressure; and a fourth switching valve connected to the fourth port of the second-mentioned switching valve and connectable to the second line, the fourth switching valve selectively fluidly connecting the second-mentioned switching valve to the source of standard pressure.

8. The apparatus of claim 3 and further comprising a mixing column connected between the second port of the first-mentioned switching valve and the detector.

9. The apparatus of claim 8 wherein the detector comprises a catalytic sensor.

10. The apparatus of claim 1 and further comprising a source of calibration gas and a second switching valve connected to the fourth port, the source of calibration gas and connectable to the source of gas, the second switching valve selectively fluidly connecting the first-mentioned switching valve to the source of calibration gas and the source of gas.

11. The apparatus of claim 1 and further comprising a second switching valve connected to the fourth port and connectable to the source of gas, the second switching valve selectively fluidly connecting the first-mentioned switching valve to a source of standard pressure and the source of gas.

12. The apparatus of claim 1 and further comprising a mixing column connected between the second port and the detector.

13. The apparatus of claim 10 wherein the detector comprises a catalytic sensor.

14. An apparatus for measuring the BTU content of a sample volume of a gas, comprising:

a source of combustion air;

a sample tube for holding a predetermined volume of the gas and having a first end and a second end;

a detector for sensing the heat content of the predetermined volume of gas;

a switching valve having multiple ports and at least two operating states, the multiple ports being connected to the first end and the second end of the sample tube and being fluidically coupleable to the source of combustion air, the gas, and the detector; and a computer providing a control signal to the switching valve to select one of the at least two operating states, the computer further receiving a signal from the detector representative of the heat content of the sample volume of gas.

15. An apparatus for measuring the BTU content of a gas, comprising:

a source of combustion air;

a sample tube for holding a predetermined volume of the gas;

a mixing device for mixing air from the source of combustion air with the predetermined volume of the gas;

a sensor for sensing the heat content of the predetermined volume of gas;

a reference sensor for sensing a temperature of the mixed combustion air and the predetermined volume of gas;

a switching valve having multiple ports and at least two operating states, the multiple ports being fluidically coupleable to the source of combustion air, the gas, the sample tube; the sensor and the reference sensor; and a computer providing a control signal to the switching valve to select one of the at least two operating states, the computer further receiving a signal from the sensor representative of the heat content of the sample volume of gas and a signal from the reference sensor representative of the temperature of the mixed combustion air and the predetermined volume of gas.

16. The apparatus of claim 15 wherein the sensor operates at a selected temperature and the reference sensor operates at the selected temperature.

17. The apparatus of claim 16 wherein the sensor comprises a catalytic sensor.

* * * * *